(12) United States Patent
Knezevic et al.

(10) Patent No.: US 6,303,808 B1
(45) Date of Patent: Oct. 16, 2001

(54) DIRECT SYNTHESIS OF TIN (II) CARBOXYLATES AND TIN(IV) CARBOXYLATES FROM ELEMENTAL TIN OR TIN OXIDES

(75) Inventors: Vasilije Knezevic, New York; Lawrence R. Brecker, Armonk, both of NY (US); Michael Fisch, Wayne; Philip J. Kleinlauth, West Milford, both of NJ (US); Radu Bacalogu, Hamburg, NY (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/635,615

(22) Filed: Aug. 10, 2000

(51) Int. Cl.⁷ ............................................ C07F 7/22
(52) U.S. Cl. ............................................... 556/105
(58) Field of Search ................................... 556/105

(56) References Cited

U.S. PATENT DOCUMENTS

| | | | | |
|---|---|---|---|---|
| 2,373,387 | * | 4/1945 | Elliot | 260/414 |
| 3,133,942 | * | 5/1964 | Hahl | 260/414 |
| 3,546,263 | * | 12/1970 | Ruf | 260/414 |
| 4,060,535 | * | 11/1977 | Cinco | 260/414 |
| 4,495,105 | * | 1/1985 | Miller | 260/414 |
| 5,068,373 | * | 11/1991 | Ruf | 556/105 |

* cited by examiner

*Primary Examiner*—Porfirio Nazario-Gonzalez
(74) *Attorney, Agent, or Firm*—Scully, Scott, Murphy & Presser

(57) ABSTRACT

A process for making a product containing tin (II) carboxylates of the formula $(RCOO)_{2-n}(OOCR')_n$, where each R, which may be the same or different, is hydrogen or a $C_1$–$C_{40}$ hydrocarbyl group, each R', which may be the same or different, is a $C_1$–$C_{40}$ hydrocarbyl group, and n is 0, 1, or 2 the process comprising:

(a) forming a reaction mixture by combining elemental tin, a promoter, and one or more carboxylate-containing compounds of the formula R(CO)X, where R is hydrogen or a $C_1$–$C_{40}$ hydrocarbyl group and X is a hydroxyl group, a halogen atom, or O(CO)R', where R' is a $C_1$–$C_{40}$ hydrocarbyl group;

(b) heating the reaction mixture to form heated reaction mixture;

(c) oxidizing the heated reaction mixture using an oxygen-containing gas to form an oxidized reaction mixture containing tin (II) carboxylates as well as tin (IV) carboxylates; and (d) reducing the oxidized reaction mixture with elemental tin to convert at least a portion of the tin (IV) carboxylates to tin (II) carboxylates to form the product containing tin (II) carboxylates.

36 Claims, No Drawings

DIRECT SYNTHESIS OF TIN (II) CARBOXYLATES AND TIN(IV) CARBOXYLATES FROM ELEMENTAL TIN OR TIN OXIDES

Many tin carboxylates have been synthesized in recent years and have been finding many uses, for example, as additives, reactants, and catalysts for a wide variety of products. For example, tin (II) carboxylates have been used widely as a synthesis catalyst for flexible polyurethane systems, like slab stock polyether-based flexible foams, such as mattresses, and molded flexible foams for the automobiles, furniture, and carpeting markets. In particular, tin (II) 2-ethylhexanoate (stannous 2-ethylhexanoate), tin (II) octoate (stannous octoate), and other tin (II) carboxylate salts are the standard catalysts for polyurethane systems. A survey of the catalysts normally used in industrial polyurethane chemistry and the mechanism on which their action is based can be found in A. Farkas and G. A. Mills, Advan. Catalysis, 13,393 (1962); J. H. Saunders and K. C. Frisch, Polyurethanes, Part I, Wiley-Interscience, New York, 1962, Chapter VI; and K. C. Frisch and L. P. Rumao, J. Macromol. Sci-Revs. Macromol Chem., C5 (1), 103–105 (1970). Such metal catalysts are highly active for urethane formation, increasing the rate of reaction of the isocyanate group with the hydroxyl group of the polyether or polyester. In addition, such tin (II) carboxylates have been used as catalysts for other reactions (see, for example, Cook, U.S. Pat. No. 3,716,523, entitled Low Concentration Stannous Carboxylate Catalysis of Polyesterification, issued Feb. 13, 1973). Tin (II) carboxylates have also been used to prepare a tin (IV) oxide catalyst for converting carbon monoxide and oxygen to carbon dioxide (Kolts, U.S. Pat. No. 5,071,818, entitled Process for Preparation of Tin Dioxide Containing Catalyst Composition, issued Dec. 10, 1991).

In addition, certain tin compounds are known to be used to treat cracking catalysts conventionally employed in the catalytic cracking of hydrocarbons for the production of gasoline, motor fuel, blending components, and light distillates. While the presence of certain metals on such catalysts can be beneficial, the presence of others is detrimental, and it is possible to passivate those deleterious metals by treating the contaminated catalyst with compounds containing antimony, tin, indium or bismuth (see, for example, U.S. Pat. Nos. 4,495,105 and 4,257,919). Tin compounds are particularly useful as passivating agents for vanadium, especially tin (II) dodecanoate and tin (II) octadecanoate.

Such tin (II) carboxylates (stannous carboxylates) are commercially produced using a chloride-based process. This can consist of reacting stannous chloride with sodium carboxylates to produce stannous carboxylates, by reacting stannic chloride with tin metal to form stannous chloride which then reacts with sodium carboxylates to form stannous carboxylates or by reacting Sn metal with aqueous HCl to produce stannous chloride which then reacts with sodium carboxylates to form stannous carboxylates. These commercial methods, which necessarily involve tin chlorides (or other halides) produce a product which contains chloride impurities, which may interfere with its ultimate use and requires the use of hydrochloric acid or chlorine gas.

A method for the preparation of tin (II) acetate is disclosed in the literature; for example, Gmelin, $8^{th}$ Ed., 1975, No. 46, Part C 2, pp. 220–221 discloses the reaction of metallic tin and glacial acetic acid wherein the reaction is permitted to proceed for 80 to 90 hours under reflux conditions and in an inert gas atmosphere. Tin (II) acetate is the sole reaction product.

Miller, U.S. Pat. No. 4,495,105, entitled Preparation of Higher Tin Carboxylates on Improved Yields Using an Inert Gas, issued Jan. 22, 1985, relates to a process for preparing tin carboxylates of higher carboxylic acids by: (a) reacting either tin (II) oxide or tin (IV) oxide with an anhydride of a lower organic acid, (b) reacting the product from (a) with at least one higher carboxylic acid, and (c) recovering the tin carboxylate of the higher carboxylic acid.

Ruf, U.S. Pat. No. 5,068,373, Entitled *Method for the Preparation of Anhydrous Tin—(IV)—Carboxylates*, issued Nov. 26, 1991, relates to a method of reacting metallic tin or tin (II) acetate with an excess of acetic anhydride to produce tin (IV) acetate. The tin (IV) acetate is separated from the reaction mixture and used as separated or, if desired, is subsequently converted to tin (IV) carboxylate having four or more carbon atoms by reaction with the appropriate carboxylic acid.

It is a primary object of the present invention to provide a general method for the production of tin (II) carboxylates and tin (IV) carboxylates which is economical and simple to carry out. Generally, it is an object of the invention to improve on the art of producing tin carboxylates, without the need for tin halides, other organometallic compounds, or carboxylic anhydrides. It is an object of the present invention to provide a process for preparation of higher carboxylates of tin that uses readily available reactants and affords high yields of the desired tin carboxylate. It is another object of the invention to provide a method of preparation wherein the tin carboxylate produced is substantially free of deleterious impurities and has a high level of thermal stability. These and other objects, aspects and advantages of the present invention will become apparent to those skilled in the art from the following description of the invention.

SUMMARY OF THE INVENTION

The present invention achieves these objectives and also exhibits the properties and advantages described herein.

One aspect of the present invention comprises a process for making a product containing tin (II) carboxylates of the formula $(RCOO)_{2-n}Sn(OOCR')_n$, where each R, which may be the same or different, is hydrogen or a $C_1$–$C_{40}$ hydrocarbyl group, each R', which may be the same or different is a $C_1$–$C_{40}$ hydrocarbyl group, and n is 0, 1 or 2, the process comprising:

(a) forming a reaction mixture by combining elemental tin, a promoter, and one or more carboxylate-containing compounds of the formula R(CO)X, where R is hydrogen or a $C_1$–$C_4$ hydrocarbyl group and X is a hydroxyl group, a halogen atom, or O(CO)R'—, where R' is a $C_1$–$C_{40}$ hydrocarbyl group;

(b) heating the reaction mixture to form a heated reaction mixture;

(c) oxidizing the heated reaction mixture using an oxygen-containing gas to form an oxidized reaction mixture containing tin (II) carboxylate and as well as tin (IV) carboxylates; and (d) reducing the oxidized reaction mixture with elemental tin to convert at least a portion of the tin (IV) carboxylates to tin (II) carboxylates if stannous compounds are desirable.

In certain embodiments of the invention, the number of moles of elemental tin added to the reaction mixture formed in step (a) is equal to or greater than the stoichiometric number of moles capable of reacting with the carboxylate-containing compounds of the formula R(CO)X to generate stannic or stannous compounds.

In preferred embodiments of the invention, the promoter is selected from the group consisting of: hindered phenols, peroxides, hydroperoxides and hydrocarbons that oxidize to form peroxides and hydroperoxides. Particularly preferred promoters are 4-tert-butylcatechol and 2,5-di-tert-butylhydroquinone.

In a preferred embodiment of the invention, the promoter is added neat to the reaction mixture or in a carrier. In a preferred embodiment of the invention, the carrier is a glycol, alcohol, carboxylic acid or polyglycol. Particularly preferred carriers are 2-ethyl 1-hexanoic acid and dipropylene glycol. In a preferred embodiment of the invention, the oxygen-containing gas is air.

In a preferred embodiment of the invention, the elemental tin is in a form selected from the group consisting of: ingots, bars, sheets, foils,rods, wires, chips, shavings, shot, beads, granules, mossy tin, powder, and dust. In another preferred embodiment of the invention, the oxidation step (c) is performed at from about 100° C. to about 200° C. In yet another preferred embodiment of the invention, the oxidation step (c) further comprises removing at least a portion of the water produced during step (c).

In a preferred embodiment of the invention, the process further comprises: (e)separating the unreacted elemental tin, and unreacted carboxylate-containing compounds of the formula R(CO)X from the product containing tin (II) carboxylates of formula $(RCOO)_2Sn$ to produce a purified product containing tin (II) carboxylate of formula $(RCOO)_2Sn$. In a preferred embodiment of the invention, the separation step (e) is accomplished by gravity settling, filtration and vacuum stripping the product containing tin (II) carboxylates of formula $(RCOO)_2Sn$.

In a preferred embodiment of the invention, the product containing tin (II) carboxylates of formula $(RCOO)_2Sn$ comprises at least 80% wt. % of $(RCOO)_2Sn$ more preferably at least 90 wt. % of $(RCOO)_2Sn$ even more preferably at least 95 wt. % of $(RCOO)_2Sn$, and most preferably at least 97 wt % of $(RCOO)_2Sn$.

Another aspect of the present invention comprises a process for making a product containing tin (IV) carboxylates of the formula $(RCOO)_{4-t}Sn(Y)_t$, wherein R is hydrogen or a $C_1–C_{40}$ hydrocarbyl group, Y is X as defined below or a derivative thereof, and t is 0, 1 or 2, the process comprising:

(a) forming a reaction mixture by combining elemental tin, a promoter, and one or more carboxylate-containing compounds of the formula R(CO)X, where R is hydrogen or a $C_1–C_{40}$ hydrocarbyl group and X is a hydroxyl group, a halogen atom, or O(CO)R',where R' is a $C_1–C_{40}$ hydrocarbyl group;

(b) heating the reaction mixture to form a heated reaction mixture; and (c) oxidizing the heated reaction mixture using an oxygen-containing gas to form an oxidized reaction mixture containing the tin (IV) carboxylate.

It will be appreciated by those of skill in the art from the description herein, that the instant invention produces the corresponding carboxylates from the respective carboxylic acid or anhydride; for example, a carboxylic acid of the formula $CH_3CH_2CH_2COOH$ will produce tin (II) carboxylates of formula. $(CH_3CH_2CH_2COO)_2Sn$ or tin (IV) carboxylates of formula $(CH_3CH_2CH_2COO)_{4-t}Sn(Y)_t$. In short, the R and R' moieties of the carboxylate of carboxylic acid of the formula R(CO)OH or the anhydride of formula R(CO)O(CO)R produce the corresponding tin (II) carboxylates of formula $(RCOO)_2Sn$ or tin ((IV) carboxylates of formula $(RCOO)_4Sn$. As would be appreciated by one of skill in the art, a mixture of two or more carboxylate-containing compounds of formula R(CO)X will produce a mixture of the corresponding tin (II) carboxylates or tin (IV) carboxylates, depending on the identity of the R group in the carboxylate-containing compounds of formula R(CO)X used. Furthermore, if an anhydride of formula R(CO)O(CO) R', where R and R' are different, is used, a mixture of tin (II) carboxylates of formulas $(RCOO)_2Sn$, $(R'COO)_2Sn$, and $(RCOO)Sn(OOCR')$, would be produced and a similar complex mixture of tin (IV) carboxylates having RCOO— and R'COO-groups would be produced.

As used herein, the term "elemental tin", "tin metal" or "tin" without modification means tin in the elemental state (Sn), in whatever allotropic form, that is, elemental tin comprises either or both of gray tin ($\alpha$-Sn) and white tin ($\beta$-tin), although white tin is preferred. The elemental tin may be in any appropriate bulk form, and the form of the elemental tin is preferably selected from the group consisting of: ingots, bars, sheets, foils, rods, wires, chips, shavings, shot, beads, granules, powder, and dust. Industrial grade tin generally contains impurities, most commonly lead, which generally remains in the end product but may be removed at some stage of the processing, or before processing, if desired. The elemental tin used in the processes of the instant invention will most likely be industrial grade tin, which is obtained from tin ore (cassiterite) and includes, at certain levels, impurities that were present in the ore or introduced by the processing of the ore. As would be appreciated by those of skill in the art, the use of purer grades of tin, for example, those with low levels or no lead, will result in a tin carboxylate product that contains correspondingly lower levels of lead or no lead. The instant processes work with pure tin, tin containing some impurities, and tin-containing alloys, and all such forms are embraced within the term elemental tin, tin metal, or tin, as used herein.

As used herein, the term "alkyl" refers to fully saturated linear (straight-chain) and branched hydrocarbon groups, for example, alkyl includes linear and branched methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl gruops. As used herein, the term "alkenyl"refers to linear or branched hydrocarbon groups containing at least one carbon-carbon double bond. As used herein, the term "alkynyl" refers to linear or branched hydrocarbon groups containing at least one carbon-carbon triple bond. As used herein, the terms "aliphatic" refers to linear or branched, saturated or unsaturated, hydrocarbon groups, that is, alkyl groups, alkenyl groups, and alkynyl groups. As used herein, the terms "cycloalkyl" or "cyclic alkyl" refer to fully saturated hydrocarbon groups containing one, two, three, or more cyclic rings. As used herein, the terms "cycloalkenyl" or "cyclic alkenyl" refers to hydrocarbon groups containing one, two, three, or more cyclic rings and at least one double carbon-carbon double bond in the ring, for example, a cyclohexenyl group. As used herein, the term "cycloaliphatic" refers herein to saturated or unsaturated hydrocarbon groups containing one, two, three, or more cyclic rings, that is, cycloalkyl groups and cycloalkenyl groups. As used herein, the term "aryl" refers to a group that contains one or more aromatic rings, for example, aryl includes biaryl, biphenylyl, phenyl, naphthyl, phenanthranyl, anthranyl, and two aryl groups bridged by an alkylene group. As used herein, the terms "alkaryl" or "alkylaryl" refer to an alkyl-, alkenyl- or alkynyl-substituted aryl group. As used herein, the terms "aralkyl" or "arylalkyl"

refer to an alkyl, alkenyl, or alkynyl group substituted with an aryl group. As used herein, the term "hydrocarbyl" refers to aliphatic, cycloaliphatic, aryl, alkaryl, and aralkyl groups. It should be noted that these classifications are not necessarily exclusive for a particular group; thus, a linear aliphatic group containing both a carbon-carbon double bond and a carbon-carbon triple bond may be considered an alkenyl group, an alkynyl group, or both. It is understood that cyclic structures, for example, cycloaliphatic groups and aryl groups, require at least three carbon atoms to form a ring and therefore a term such as "$C_1$ to $C_{40}$" when applied to or modifying such a cyclic structure or applied to a term, for example, hydrocarbyl, that includes such cyclic groups, is understood to actually designate only cyclic groups containing 3 to 40 carbon atoms for these cyclic groups.

As used herein, the terms "tin carboxylates" "tin halides", and similar terms that do riot indicate the oxidation state of the tin in the compound mean that both the tin (II) and tin (IV) compounds are intended to be designated thereby. In contrast, the terms "tin (II) carboxylates", "stannous chloride", "tin (IV) carboxylates", and "stannic chloride", and similar terms that indicate the oxidation state of the tin in the compound, have the common meaning known to those of skill in the art and are used where the oxidation state of the tin is an aspect of the meaning of the statement wherein the term is used. In the instant invention, a carboxylate-containing compound of formula RC(O)X, where R is hydrogen or a hydrocarbyl group, and X is a hydroxyl group, a halogen atom, or O(CO)R', where R' is hydrogen or a hydrocarbyl group, is added to the reaction mixture in step (a). It is contemplated and understood that, to the extent that a compound possess a carboxylate group or may be converted to a carboxylate group, for example, by hydrolysis, it may be considered an equivalent to the recited carboxylate-containing compound of formula RC(O)X, however, a carboxylate-containing compound of formula RC(O)X is preferred. As used herein, the term "carboxylate-containing compound" means any compound that has a carboxylate group (—C(O)O—) in the structure. The carboxylate group is found in many well-known organic species, including, without limitation, carboxylic acids, whether monocarboxylic acids, dicarboxylic acids, or polycarboxylic acids; the salts of carboxylic acids; carboxylic acid anhydrides ("anhydrides"); and esters, and each of these compounds is considered a carboxylate-containing compound.

In preferred embodiments of the invention R and R' are each independently selected from the group consisting of hydrogen and $C_1$ to $C_{40}$ aliphatic, cycloaliphatic, aryl, alkaryl, and aralkyl groups; more preferably hydrogen and $C_1$ to $C_{30}$ aliphatic, cycloaliphatic, aryl, alkaryl, and aralkyl groups; even more preferably hydrogen and $C_1$ to $C_{24}$ aliphatic, cycloaliphatic, aryl, alkaryl, and aralkyl groups; and most preferably hydrogen and $C_1$ to $C_{22}$ aliphatic, cycloaliphatic, aryl, alkaryl, and aralkyl groups. Although the aliphatic, cycloaliphatic, aryl, alkaryl, and aralkyl groups of R and R' may themselves be substituted with other groups or include other functionalities, for example; halogen substituents or ether functionalities, in preferred embodiments of the invention, R and R' are selected from aliphatic, cycloaliphatic, aryl, alkaryl, and aralkyl groups that are not so substituted or functionalized.

When X represents a chloride or bromide atom a mixed carboxylate chloride or bromide are formed with the general formula $(RCOO)SnCl$ or $(RCOO)SnBr$ and $(RCOO)_2SnCl_2$ or $(RCOO)_2SnBr_2$.

The reduction step occurs when-reducing conditions, which are temperature-dependent, are present. Generally such a reduction step occurs in the absence of the oxygen or when there are low levels of oxygen present, either because the oxygen-containing gas has been partially or completely depleted of oxygen during reaction or because the oxygen and/or oxygen-containing gas is partially or completely removed by vacuum or displaced by an inert gas, such as nitrogen, carbon dioxide, or a noble gas.

Examples of organic tin salts made in accordance with the invention are tin (II) acetate, tin (II) octoate, tin (II) 2-ethyl hexanoate, tin (II) oleate, tin (II) laurate, tin (II) adipate, tin (II) oxalate, tin (II) succinate, tin (II) phthalate, tin (II) benzoate, tin (II) naphthenate, tin (II) butyrate, tin (II) hexanoate, and the like. The catalysts may be used either individually or in any combination. In addition, such tin salts may be further combined with a tertiary amine because synergism in regard to the catalytic activity is frequently observed in this case.

DETAILED DESCRIPTION OF THE INVENTION

The present invention is directed to a novel process for synthesizing tin carboxylates and the tin carboxylates produced by such method. The invention provides a general method for the production of tin (II) carboxylates and tin (IV) carboxylates which is economical and straightforward.

In contrast to prior art processes, the instant process does not use or produce a metal halide as an intermediate or starting material. Futhermore, the instant process does not employ any organometallic compounds for a metal substitution reaction or use cumbersome reaction conditions employed in the direct reaction of the metal and the carboxylic acid. Although not to be bound to any particular theory, it is hypothesized that the instant method proceeds through a tin oxide intermediate formed by air oxidation of the metal in bulk form (for example, metal shot, shavings, or powder) that is not produced in any of the prior art methods.

The instant method eliminates the use of chlorides or halides by producing metal carboxylates directly from the bulk metal, which generally results in lower production costs. All of the traditional industrial processes for making tin carboxylates use tin chlorides or halides as a starting material and the products therefore contain high levels of the non-tin ions produced in the process, generally sodium ($Na^+$) and chloride($Cl^-$). The presence of high levels of sodium and chloride in commercial tin carboxylate products indicates that such products have been produced using a stannous chloride or stannic chloride processing route. As the instant invention does not proceed through or otherwise use tin halide, in comparison with the tin carboxylate produced by traditional tin halide synthesis processes, the processes of the instant invention contain comparatively low levels of non-tin salts in the ultimate product (and contain moderate levels of lead, which depends on the amount of lead in the elemental tin used in the process). In general, the metal may be used in any form, whether ingots, bars, sheets, foils, rods, wires, chips, shavings, shot, beads, granules, powder, dust, liquid, or the like, although certain forms, as explained below, may be preferred.

High production costs are associated with using chloride-based processes to synthesize stannous carboxylates due to the high raw material cost of making stannous chloride (which is not needed in the instant process) and the high production costs from washing the stannous carboxylate products to reduce the sodium and chloride levels. The instant process produces the tin carboxylates directly from tin metal and therefore has much lower raw material cost.

Furthermore, stannous carboxylates produced directly from tin metal are much lower in sodium and chloride than tin chloride-based processes without the need of water washing. Moreover, the instant direct process poses no corrosion problems for equipment by avoiding the use of tin chlorides and consequently the formation of hydrogen chloride from hydrolysis.

Although detailed synthesis procedures for each of these steps are set forth below in detail, it should be understood that all of these procedures are exemplary and the invention is not limited to the examples set forth below. As would be appreciated by those of skill in the art, many different synthesis, separation, and analysis methods and different apparatus and equipment are known to those of skill in the art which would produce similar or the same results as the exemplary procedures and methods used below. It is therefore expected that the exemplary procedures set forth below may be modified, supplemented, or substituted with other methods known to those of skill in the art without departing from the spirit of the invention or the disclosure herein. For example, the batch procedure set forth herein may be modified and optimized to obtain a continuous process where the reactants are continually added and the heating, oxidizing, reducing, and separation steps are carried out continuously in an apparatus or series of apparatuses. All such procedures and methods are intended to be covered by the appended claims.

SYNTHESIS OUTLINE AND EXAMPLES

Tin carboxylates, such as stannous carboxylate, are produced by charging to a reactor an excess of tin metal shot or powder, the carboxylic acid, and a promoter, such as 4-tert-butylcatechol or 2,5-di-tert-butylhydroquinone, generally added neat or in a carrier such as a diol or glycol or carboxylic acid, for example, dipropylene glycol and 2-ethyl-1-hexanoic acid. The amount of promoter is 1 to 20% of the tin metal charged, preferably 1–2%. Other similar compounds such as hindered phenols, peroxides, hydroperoxides, and hydrocarbons that oxidize to form peroxides and hydroperoxides can also be used as promoters. This reaction mass, if at room temperature, is heated, for example, to 60° C. and an oxygen-containing gas, such as air, is introduced. The temperature of the reaction mass is then generally raised to between 140° C. to 180° C., although the heat of reaction will also raise the temperature.

If a tin (IV) carboxylate product is desired, the oxidation is allowed to proceed until a selected endpoint is reached, for example, a 5–20% total tin level of the product is achieved, preferably 10–15% and 60–90%, preferably 85–90% of the total tin is of the stannic type; the oxidation step is then deemed completed and the product mixture is recovered. Separation of the tin (IV) carboxylate from unreacted tin, reactants, tin oxides, and tin (II) carboxylate, if desired, is then performed to recover a purified tin (IV) carboxylate product.

If a tin (II) carboxylate product is desired, the oxidation is continued until a selected end-point is reached, for example, a 5–20% total tin level of the product is achieved, preferably 10–15% and 60–90% preferably 85–90% of the total tin is of the stannous type. At such an end-point, the temperature is maintained, for example, at 140–170° C., and an inert gas, such as nitrogen, is introduced to the reaction mass in place of the oxygen-containing gas. The term "inert gas" as used herein means a gas that will not react with the reaction mass, and includes, without limitation, nitrogen gas, helium gas, neon gas, argon gas, krypton gas, and the like.

During this reduction or disproportionation step of the process, the inert gas flow is kept constant until the desired end-point is reached. The reaction mass may then be purified or subjected to a separation procedure, for example, by filtering the reaction product and stripping under vacuum to remove the unreacted acid. If required, a second filtration is done to remove any unreacted tin and stannous or stannic oxide.

In general, the form of the tin metal used influences the reaction conditions used in the instant process: the more finely divided forms of tin metal (e.g., powder) have greater surface area and are more reactive than tin shot or tin ingots, allowing for more gentle reaction conditions to be used. For example, the use of tin powder instead of tin shot to synthesize stannous carboxylates according to the instant invention, allows the oxidation step of the tin powder synthesis to be run at a lower temperature (e.g., 100° C.–120° C.), than the 140° C.–180° C. required for the tin shot synthesis; and, indeed, such lower temperatures may result in lighter colored tin carboxylate products, which may be more commercially desirable.

Washes may be used to remove the promoter (for example, 4-tert-butylcatechol) and allow lower distillation conditions by azeotroping the water and 4-tert-butylcatechol off, although a well-designed stripper or other separation method may eliminate the need for these washes, Additionally, any processing steps requiring separation can employ any of the separation methods known in the art, depending on which methods are the most economical and produce the best quality product (for example, gravity settling, filtration, centrifugation, etc.). For example, white mineral oil has been used prior to the stripping off of the carboxylic acids in order to facilitate easier removal of the excess acids, which helps reduce processing costs associated with distillation.

Although the stannous/stannic tin ratios and total tin measurements were made by iodometric wet method titrations, any suitable analytical method may be used including manual and automated potentiometric titrations, X-ray fluorescence analysis, IR analysis, or colorimetry measurements.

Important parameters in the synthesis are the use of an excess of tin metal and promoter. The promoter (e.g., 4-tert-butylcatechol) promotes the oxidation of tin metal to stannous oxide/stannous carboxylate during the oxidation step and is also necessary, along with excess tin metal, during the reduction step to promote the formation of stannous carboxylate. Thus, the promoter appears to act as a catalyst for the formation of stannous carboxylate and at the same. time it acts as an inhibitor for oxidation of stannous tin during the reduction/disproportionation step.

SYNTHESIS EXAMPLES

Example 1

Stannous 2-ethylhexanoate from Tin Shot

To a two liter reactor were charged 500 grams of tin shot, 1250 grams of 2-ethyl-1-hexanoic acid, 15 grams of 4-tert-butylcatechol and 15 grams of dipropylene glycol and the mixture was heated to 60° C. Air was introduced below the surface of the reaction mass and the reaction mixture heated to 155–170° C. After four hours of oxidation, analysis of the reaction mixture indicated 15.1% stannous and 16.7% total tin. The reaction mass was then heated to 165° C. and the air replaced with nitrogen gas. After 1.5 hours, analysis of the reaction mass revealed 17.3% stannous and 17.4% total tin. The reaction mixture was decanted of unreacted tin shot and then stripped under vacuum (2–5 mmHg) at 165° C. to remove the unreacted 2-ethyl-1-hexanoic acid and then filtered using filter aid. The filtered product contained 28.5% stannous and 28.7% total tin. The final material balance was as follows: 758 grams of stannous 2-ethylhexanoate, 222 grams unreacted tin shot, and 711 grams of unreacted 2-ethyl-1-hexanoic acid.

Example 2

Stannous 2-ethylhexanoate from Tin Powder and Tin Shot

To a 6 liter reactor were charged 400 grams of tin powder, 1600 grams of tin shot, 3000 grams of 2-ethyl-1-hexanoic acid, and 10 grams of 4-tert-butylcatechol. The mixture was heated to 60° C. and air introduced below the surface of the mixture. The reaction temperature was then maintained at 80° C. to 120° C. for 10 hours, and the stannous content was analyzed as 86% of the total tin (15%). The air was then replaced with nitrogen gas, and 15 grams of dipropylene glycol added. The reaction temperature of the mixture was maintained at 155° C. for two hours, until 98.3% of the total tin was stannous. The reaction mass was then decanted of unreacted tin and filtered to remove small amounts of stannous oxide. The reaction mass was then stripped under 2 mm Hg vacuum at 145° C. to obtain 1812 grams of stannous octoate product having 28% stannous tin and 29% total tin.

Example 3

Stannous Oleate

To a one liter reactor was charged 500 grams of oleic acid, 150 grams of tin shot, and 1.5 grams of 4-tert-butylcatechol. This reaction mixture was heated to 80° C., and air introduced. The reaction temperature was gradually raised to 140° C. until a level of 15% stannous tin was reached. The mixture was then filtered to remove any unreacted stannous oxide to form 575 grams of product.

Example 4

Stannous Stearate

To a one liter reactor was charged 130 grams of tin shot, 20 grams of tin powder, 330 grams of stearic acid, and 5 grams of 4-tert-butylcatechol. This reaction mixture was heated to 80° C., and air introduced. The reaction temperature was gradually raised to 140° C. until a level of 13.4% stannous tin and 17.6% total tin was reached. The air was then replaced with nitrogen and the temperature was raised from 140° C. to 160° C. After two hours the reaction mixture contained 16.2% stannous and 17.6% total tin. The reaction mass was decanted of unreacted tin then filtered at 140° C. to form 398 grams of product.

Example 5

Stannous Coconutate

To a one liter reactor was charged 225 grams of tin shot, 600 grams of coconut acid, and 5 grams of 4-tert-butylcatechol. This reaction mixture was heated to 80° C., and air introduced. The reaction mass was heated to 140–160° C. and the stannous level reached 14.5% and the total tin was 17.5%. Air was then replaced with nitrogen and the reaction continued until a stannous level of 21.8% and a total tin of 22.3% was reached. The reaction mass was then decanted of unreacted tin shot and filtered to form 770 grams of product.

The tin carboxylates made by the instant process typically contain 97% stannous tin. These tin products all have chloride levels below 50 ppm, often less than 20 ppm, while sodium levels are typically less than 50 ppm, often less than 10 ppm. In contrast, commercial samples of tin (II) octoate, which are presumably made by a tin chloride intermediate, typically have chloride levels above 80 ppm, sometimes more than 2000 ppm, while sodium levels are typically more than 380 ppm, often more than 2000 ppm.

It is also understood that the efficiency of the basic process can be enhanced by recycling unused or unreacted portions of the metal or carboxylic acid. It is also understood that the basic batch process can be modified to the respective continuous process with realization of expected economic and process efficiencies.

As noted above, the examples provided are intended to further describe the aspects of the present invention. The examples are illustrative only and are not to be construed as limiting the scope of that which is regarded as the invention. Therefore, the scope of the present invention is only to be limited by the following claims and the equivalents thereto.

What is claimed is:

1. A process for making a product containing tin (II) carboxylates of the formula $(RCOO)_{2-n}Sn(OOCR')_n$, where each R, which may be the same or different is hydrogen or a $C_1$–$C_{40}$ hydrocarbyl group, each R' which may be the same or different, is a $C_1$–$C_{40}$ hydrocarbyl group, and n is 0, 1 or 2, the process comprising:

(a) forming a reaction mixture by combining elemental tin, a promoter, and one or more carboxylate-containing compounds of the formula R(CO)X, where R is hydrogen or a $C_1$–$C_{40}$ hydrocarbyl group and X is a hydroxyl group, a halogen atom, or O(CO)R', where R' is a $C_1$–$C_{40}$ hydrocarbyl group;

(b) heating the reaction mixture to form a heated reaction mixture;

(c) oxidizing the heated reaction mixture using an oxygen-containing gas to form an oxidized reaction mixture containing tin (II) as well as tin (IV) carboxylates; and (d) reducing the oxidized reaction mixture with elemental tin to convert at least a portion of the tin (IV) carboxylates to tin (II) carboxylates to form the product containing tin (II) carboxylates.

2. The process according to claim 1, wherein the number of moles of elemental tin added to the reaction mixture formed in step (a) is equal to or greater than the stoichiometric number of moles capable of reacting with carboxylate-containing compounds of the formula R(CO)X to form stannous compounds.

3. The process according to claim 1, wherein the promoter is selected from the group consisting of:
hindered phenols, peroxides, hydroperoxides and hydrocarbons that oxidize to form peroxides and hydroperoxides.

4. The process according to claim 1, wherein the promoter is 4-tert-butylcatechol or 2,5-di-tert-butylhydroquinone.

5. The process according to claim 1, wherein the promoter is added to a carrier prior to being added to the reaction mixture.

6. The process according to claim 5, wherein the carrier is a glycol, alcohol, or polyglycol.

7. The process according to claim 6, wherein the carrier is dipropylene glycol.

8. The process according to claim 1, wherein the oxygen-containing gas is air.

9. The process according to claim 1, wherein the elemental tin is in a form selected from the group consisting of: ingots, bars, sheets, foils, rods, wires, chips, shavings, shot, beads, granules, powder, and dust.

10. The process according to claim 1, wherein the oxidation step (c) is performed at from about 100° C. to about 200° C.

11. The process according to claim 1, wherein the oxidation step (c) further comprises removing at least a portion of the water produced during step (c).

12. The process according to claim 1, further comprising:
  (e) separating the promoter, unreacted elemental tin, and unreacted carboyxiate-containing compounds of the formula R(CO)X from the product containing tin (II) carboxylates to produce a purified product containing tin (II) carboxylates.

13. The process according to claim 12, wherein the separation step (e) is accomplished by washing the product containing tin (II) carboxylates with water.

14. The process according to claim 1, wherein the product containing tin (II) carboxylates comprises at least 80 wt. % of stannous carboxylates.

15. The process according to claim 14, wherein the product containing tin (II) carboxylates comprises at least 90 wt. % of stannous carboxylates.

16. The process according to claim 15, wherein the product containing tin (II) carboxylates comprises at least 95 wt. % of stannous carboxylates.

17. The process according to claim 16, wherein the product containing tin (II) carboxylates comprises at least 97 wt. % of stannous carboxylates.

18. A process for making a product containing tin (IV) carboxylates of the formula $(RCOO)_{4-t}Sn(Y)_t$, wherein R is hydrogen or a $C_1$–$C_{40}$ hydrocarbyl group, Y is X, as defined below, or a derivative thereof, and t is 0, 1 or 2, the process comprising:
  (a) forming a reaction mixture by combining elemental tin, a promoter, and one or more carboxylate-containing compounds of the formula R(CO)X, where R is hydrogen or a $C_1$–$C_{40}$ hydrocarbyl group and X is a hydroxyl group, a halogen atom, or O(CO)R', where R' is a $C_1$–$C_{40}$ hydrocarbyl group;
  (b) heating the reaction mixture to form a heated reaction mixture; and
  (c) oxidizing the heated reaction mixture using an oxygen-containing gas to form an oxidized reaction mixture containing the tin (IV) carboxylates.

19. The process according to claim 18, wherein the number of moles of elemental tin added to the reaction mixture formed in step (a) is equal to or greater than the stoichiometric number of moles capable of reacting with the carboxylate-containing compounds of the formula R(CO)X to generate stannic compounds.

20. The process according to claim 18, wherein the promoter is selected from the group consisting of:
  hindered phenols, peroxides, hydroperoxides and hydrocarbons that oxidize to form peroxides and hydroperoxides.

21. The process according to claim 18, wherein the promoter is 4-tert-butylcatechol or 2,5-di-tert-butylhydroquinone.

22. The process according to claim 18, wherein the promoter is added to a carrier prior to being added to the reaction mixture.

23. The process according to claim 22, wherein the carrier is a glycol, alcohol, or polyglycol.

24. The process according to claim 23, wherein the carrier is dipropylene glycol.

25. The process according to claim 18, wherein the oxygen-containing gas is air.

26. The process according to claim 18, wherein the elemental tin is in a form selected from the group consisting of: ingots, bars, sheets, foils, rods, wires, chips, shavings, shot, beads, granules, powder, and dust.

27. The process according to claim 18, wherein the oxidation step (c) is performed at from about 100° C. to about 200° C.

28. The process according to claim 18, wherein the oxidation step (c) further comprises removing at least a portion of the water produced during step (c).

29. The process according to claim 18, further comprising:
  (d) separating the promoter, unreacted elemental tin, and unreacted carboxylate-containing compounds of the formula R(CO)X from the product tin (IV) carboxylates to produce a purified product containing tin (IV) carboxylates.

30. The process according to claim 29, wherein the separation step (d) is accomplished by washing the product containing tin (IV) carboxylates with water.

31. The process according to claim 30, wherein the product containing tin (IV) carboxylates comprises at least 80 wt % of tin (IV) carboxylates.

32. The process according to claim 31, wherein the product containing tin (IV) carboxylates comprises at least 90 wt. % of tin (IV) carboxylates.

33. The process according to claim 32, wherein the product containing tin (IV) carboxylates comprises at least 95 wt. % of tin (IV) carboxylates.

34. The process according to claim 33, wherein the product containing tin (IV) carboxylates comprises at least 97 wt. % of tin (IV) carboxylates.

35. A product containing the tin (II) carboxylates of the formula $(RCOO)_2Sn$ produced by the process of claim 1.

36. A product containing the tin (IV) carboxylates of the formula $(RCOO)_4Sn$ produced by the process of claim 18.

* * * * *